US008748848B1

(12) United States Patent
Li et al.

(10) Patent No.: US 8,748,848 B1
(45) Date of Patent: Jun. 10, 2014

(54) METHOD OF GENERATING RAMAN LASER FOR INDUCING FLUORESCENCE OF FLUORANTHENE AND A SYSTEM THEREOF

(71) Applicant: Macau University of Science and Technology, Taipa (MO)

(72) Inventors: Jianqing Li, Taipa (MO); Ben Xu, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 13/933,140

(22) Filed: Jul. 2, 2013

(51) Int. Cl.
*G01N 21/64* (2006.01)
*G01N 21/65* (2006.01)

(52) U.S. Cl.
CPC .................... *G01N 21/65* (2013.01)
USPC ...................................... 250/459.1

(58) Field of Classification Search
CPC .............................. G01N 2021/1793
USPC ...................................... 250/459.1
See application file for complete search history.

(56) References Cited

U.S. PATENT DOCUMENTS 6,025,200 A * 2/2000 Kaish et al. ............... 436/56
6,696,157 B1 * 2/2004 David et al. ............... 428/408

FOREIGN PATENT DOCUMENTS

CN 201010587603 7/2012

OTHER PUBLICATIONS

Pask et al., "Wavelength-versatile visible and Uv sources based on crystalline Raman lasers," 2008, Progress in Quantum Electronics, vol. 32, pp. 121-158.*

* cited by examiner

*Primary Examiner* — Kiho Kim
(74) *Attorney, Agent, or Firm* — EAGLE IP Ltd.; Jacqueline C. Lui

(57) ABSTRACT

A method of generating Raman laser for inducing fluorescence of fluoranthene and a system thereof is disclosed. The system comprising a pulsed laser, a frequency doubling crystal, a frequency quadrupling crystal, a light filter unit, a quarter-wave plate, a Raman cell filled with deuterium gas( ), a light dispersion device and an optical diaphragm. The method of the present invention comprises the steps of emitting a laser beam pulse through the crystals as mentioned above such that a mixture of lasers is generated. The light filter unit and the quarter-wave plate are used to obtain a circular or ellipsometric polarized pump laser from the mixture of lasers. Finally, the Raman laser is obtained by directing the pump laser into a Raman cell filled with deuterium gas, extracting different orders of stimulated Raman scattering lasers emitted from the Raman cell by the light dispersion device and selecting the desired order of stimulated Raman scattering laser by the optical diaphragm.

12 Claims, 2 Drawing Sheets

METHOD OF GENERATING RAMAN LASER FOR INDUCING FLUORESCENCE OF FLUORANTHENE AND A SYSTEM THEREOF

FIELD OF INVENTION

This invention relates to a method of generating Raman laser for inducing fluorescence of fluoranthene; and a system for generating Raman laser for inducing fluorescence of fluoranthene.

BACKGROUND OF INVENTION

Fluoranthene is a type of polycyclic aromatic hydrocarbons (PAHs), which hardly degrades in natural environment, lasts for a long period of time and exhibits carcinogenicity, mutagenicity and teratogenicity. Hence detection of PAHs is of great concern and many countries have listed PAHs as one of the priority pollutants. PAHs in water mainly come from atmospheric deposition, urban sewage, discharges of industrial wastewater, and oil leakage etc. The PAHs polluted water eventually enters into surface water and groundwater causing contamination of drinking water source. Since PAHs is hydrophobic and highly un-degradable, it usually exists in water at a low concentration. As a result, detection of PAHs is a complex and important measurement analysis issue. Among different PAHs, fluoranthene has higher fluorescence quantum efficiency and thus can be detected using fluorescence methods.

The fluorescence spectroscopy of fluoranthene requires a suitable excitation source in order to obtain strong fluorescence intensity for signal detection. The Anhui Institute of Optics and Fine Mechanics of Chinese Academy of Sciences identified two relative strong fluorescence emission zones of fluoranthene utilizing F-7000 type fluorescence spectrophotometer. One of the emission peak of the fluorescence intensity is $\lambda_{ex}/\lambda_{em}=286/462$ nm (as shown in FIG. 1), where $\lambda_{ex}$ and $\lambda_{em}$ denote the wavelengths of excitation and emission light, respectively. Therefore, the wavelength of the excitation light source is preferably to be 286 nm, or any neighbouring values.

The simplest way to obtain an excitation light source with such excitation wavelength is to apply a spectrometer or spectrophotometer, which utilizes spectral elements such as prisms or gratings to split a continuous spectrum light source in order to isolate an excitation light with desired wavelength. This method is simple and direct, but the disadvantage is that the intensity of the output light is very low. Also the above method generally requires sampling and testing of the spectrometer or spectrophotometer, which is not convenience while the device is in operation, which limits its use.

Tunable laser source is another alternative. Tunable laser sources have a certain wavelength tuning range and the intensity of the output laser can usually fulfil the test requirements. However, the cost of the tunable laser source is high, which costs several millions Renminbi, and thus is not popular. Moreover, if a tunable dye laser source is used, the carcinogenic dye in the tunable dye laser source will be a threat against the health of the users.

The United States Environmental Protection Agency utilized a laser-fluorescence embedded cone penetrometer system mounted on a vehicle to detect the fluoranthene content in soil. The excitation light for inducing fluorescence of fluoranthene of the above mentioned system is generated by emitting a Nd:YAG fourth harmonic laser through a Raman cell filled with a gas mixture comprising methane ($CH_4$) and hydrogen ($H_2$) gas. As a result, the first stokes radiation of $CH_4$ at 288.4 nm is produced, and it is stable and closed to the excitation peak 286 nm of the preferred excitation light for fluorescence detection of fluoranthene. But the drawback is that $CH_4$ decomposes easily due to the long stimulated time of $CH_4$ by the Nd:YAG fourth harmonic laser

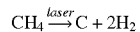

(The Anhui Institute of Optics and Fine Mechanics of Chinese Academy of Sciences has conducted similar experiment and reported this phenomena with detailed analysis). As a result, micro-carbon granules (with diameters of tens to hundreds of microns) will be generated, which will attach to the glass windows at both ends of the Raman cell and reduce the transmittance of the Raman cell. Moreover, the decomposition process reduces the $CH_4$ content in the Raman cell which in turn reduces the intensity of the output of the first stokes radiation (288.4 nm).

Therefore there is a need to develop a low-cost, yet stable laser source with suitable wavelength.

SUMMARY OF INVENTION

The first objective of the present invention is to provide a method of making stable, low-cost, high intensity Raman laser for inducing fluorescence of fluoranthene which overcomes the existing technical limitations.

The second objective of the present invention is to provide a system for generating Raman laser for inducing fluorescence of fluoranthene.

In one aspect of the present invention, a method of generating Raman Laser for inducing fluorescence of fluoranthene comprising the steps of: emitting a laser beam pulse; transmitting the laser beam pulse through a frequency doubling crystal and a frequency quadrupling crystal thereby generating a mixture of lasers; extracting a pump laser from the mixture of lasers with different wavelengths; passing the pump laser through a quarter-wave plate to change the polarization status of the pump laser; providing a Raman cell filled with predetermined gas at a predetermined pressure; directing the pump laser into the Raman cell thereby exciting different orders of stimulated Raman scattering lasers; selecting a predetermined order of the stimulated Raman scattering laser.

In one embodiment, the predetermined gas is deuterium gas ($D_2$) and the predetermined pressure is ranged from 0.8-1.0 MPa.

In another embodiment, the selecting step further comprises the step of splitting said different orders of stimulated Raman scattering laser.

In another aspect of the present invention, a system of generating Raman laser for inducing fluorescence of fluoranthene comprising a pulsed laser source configured to emit a laser beam pulse; a frequency doubling crystal and a frequency quadrupling crystal for the laser beam pulse to pass thorough thereby generating a mixture of lasers with different wavelengths; a light filter unit configured to extract a pump laser from the mixture of laser; a quarter-wave plate configured to change the polarization status of the pump laser; a Raman cell filled with predetermined gas at a predetermined pressure configured to generate different orders of stimulated Raman scattering lasers upon interact with the pump laser; a light dispersion device configured to split the different orders of stimulated Raman scattering lasers spatially; and an optical diaphragm configured to select predetermined order of the stimulated Raman scattering laser from the different orders of stimulated Raman scattering lasers.

In one embodiment, the pulsed laser source is a Nd:YAG pulsed laser source.

In yet another embodiment, the light filter unit further comprises a first light filter and a second light filter, wherein each the first light filter and the second light filter comprises a mirror-like surface which is reflective to the pump laser.

In yet another embodiment, the light dispersion device further comprises at least two prisms configured to receive and spatially separate different orders of stimulated Raman scattering lasers.

The present invention has the following advantages comparing with the existing technologies:

The Raman wavelength as provided by the method proposed by the present invention locates exactly at the excited peak of the fluoranthene spectrum. Therefore it improves the accuracy of the detection and the stability of the system for fluorescence spectroscopy of fluoranthene. Moreover, the Raman cell of the present invention is low cost, which does not involve any thermal decomposition reaction, yet stable even after long working hours. The method and system of the present invention thus improves the reliability of the generation of the Raman laser.

DETAILED DESCRIPTION OF THE PREFERRED EMBODIMENTS

The present invention is illustrated with the combination of the figures and the following embodiments.

Figure 1:
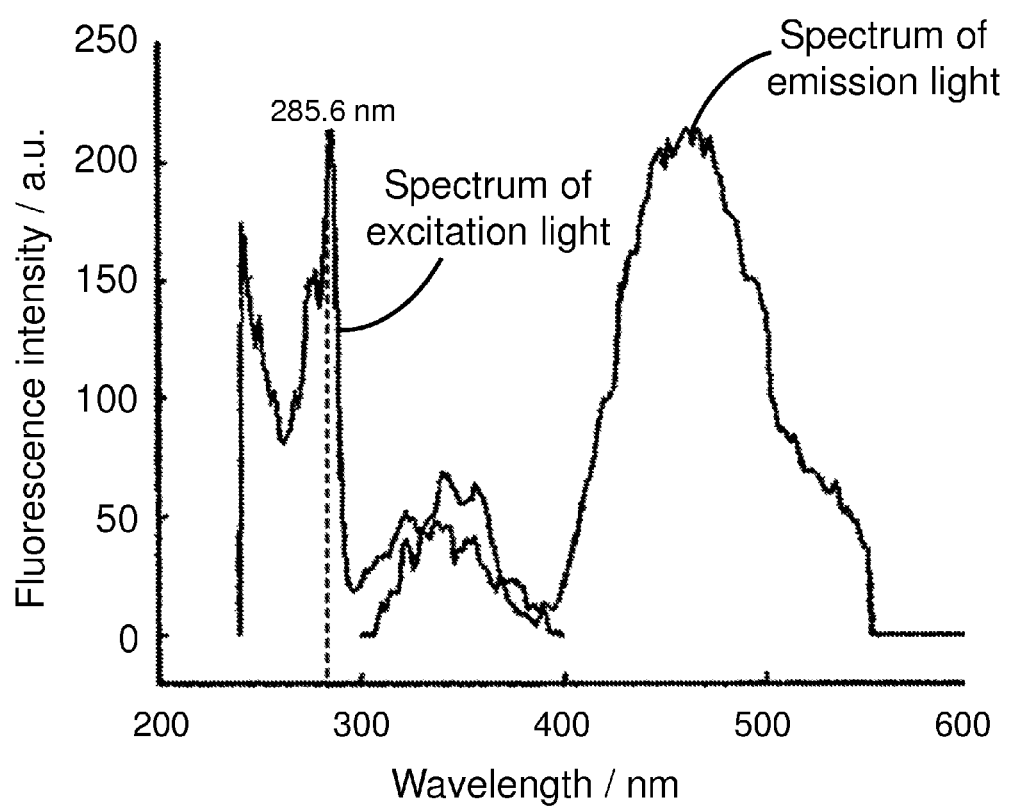
FIG. 1 shows the spectrum of excitation light and corresponding emission light for fluorescence detection of fluoranthene respectively.

FIG. 1 shows the spectrum of the excitation light and corresponding emission light for fluorescence detection of fluoranthene respectively. As shown in FIG. 1, the Raman laser has peak intensity at 285.6 nm, which is very close to the preferred wavelength of the laser light source (i.e. 286 nm), which results in strong fluorescence intensity of fluoranthene at around 462 nm.

Figure 2:
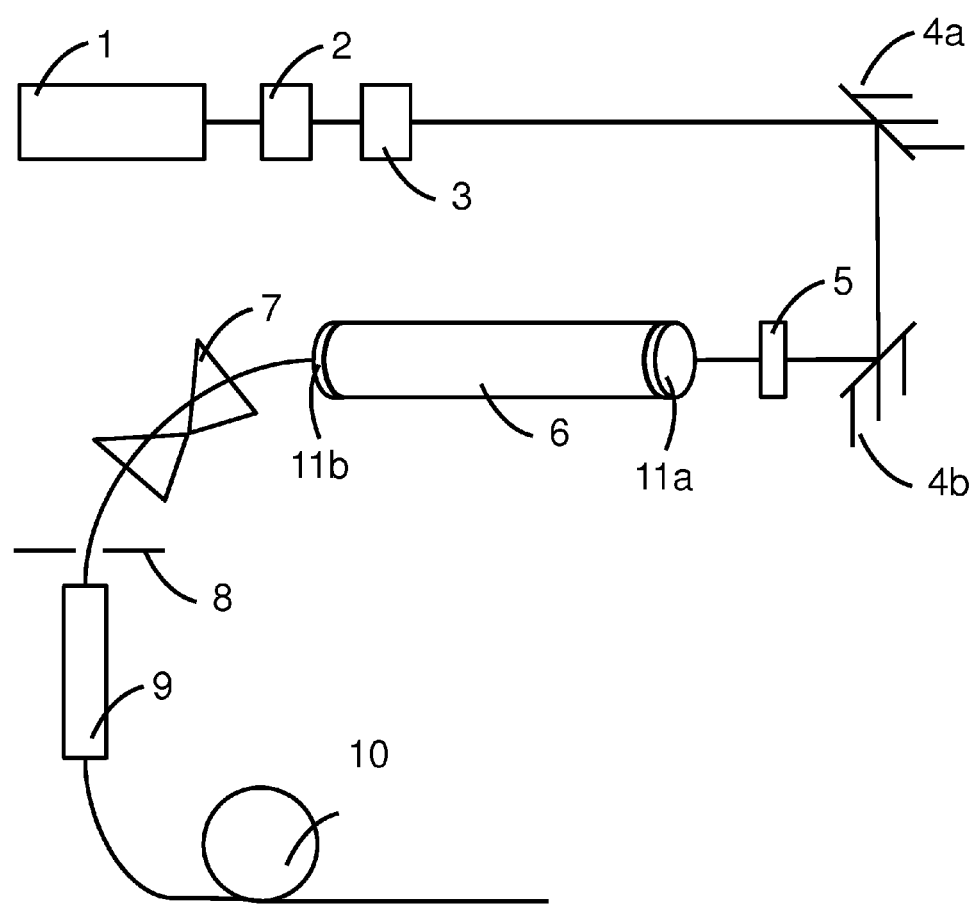
FIG. 2 is a schematic diagram of the system of generating Raman laser for inducing fluorescence of fluoranthene according to one of the embodiment of the present invention.

Referring to FIG. 2, the schematic diagram of a system of generating Raman laser for inducing fluorescence of fluoranthene according to one embodiment of the present invention is shown. The system comprises a Nd:YAG pulsed laser source 1; a frequency doubling crystal 2; a frequency quadrupling crystal 3; a light filter unit 4; a quarter-wave plate 5; a Raman cell 6; a light dispersion device 7; an optical diaphragm 8; a convex lens 9 and an optical fiber 10. Two convex lens 11a and 11b are installed at the two ends of the Raman cell 6 acting as its two windows.

In one embodiment, the frequency doubling crystals 2 is made of material selected from a group consisting of KDP crystal, KD*P crystal and BBO crystal. In another embodiment, the frequency quadrupling crystal 3 is made of BBO crystal.

The light filter unit 4 used in one embodiment of the present invention comprises a first light filter 4a and a second light filter 4b. Each of the light filters 4a and 4b comprises a mirror face and the light filters 4a and 4b are disposed such that the mirror faces are perpendicular to each other. The incident angle of the laser generated by the Nd:YAG pulsed laser source 1 is 45° relative to the mirror faces of the first light filter 4a. The light filter unit 4 are highly anti-reflective to laser with wavelength of 1064 nm and 532 nm; but highly reflective to fourth harmonic laser with wavelength of 266 nm. The quarter-wave plate 5 is used to convert the linear polarized fourth harmonic laser at 266 nm into a circular or ellipsometric polarized laser. In one embodiment of the present invention, the quarter-wave plate is made of material selected from a group consisting of quartz and mica. The Raman cell 6 is highly pressurized at a predetermined internal pressure. In one embodiment, the Raman cell 6 is filled with deuterium ($D_2$). In another embodiment, the internal pressure of the Raman cell 6 is 0.8-1.0 MPa. In one embodiment, the light dispersion device 7 comprises a plurality of prisms configured to spatially separate the laser with desired wavelength from lasers with other wavelengths. Using multiple prisms would result in better light splitting result and reduce the size of the overall light source system by reducing the separation between the light dispersion device 7 and the convex lens 9. However, using multiple prisms would result in greater energy loss. Therefore, the actual number of prisms used would depend on the allowable size of the measurement system and the sensitivity of the subsequent detectors. In one embodiment, the light dispersion device 7 comprises two prisms. In another embodiment, the two prisms are triangular in shape and in contact at the one of the angles with an adjustable angle between two surfaces of the prisms facing each other. In another embodiment, the light dispersion device 7 comprises pentagonal prism. In yet another embodiment, the light dispersion device 7 comprises three prisms which allow further reduction in size of the light source system. The optical diaphragm 8 is configured to select the laser with wavelength of interested. In one embodiment, the laser with wavelength of 285.6 nm is selected.

Now turn to the method of generating Raman laser for inducing fluorescence of fluoranthene and the operation of the system of generating Raman laser for inducing fluorescence of fluoranthene according to one embodiment of the present invention.

First, the Nd:YAG pulsed laser source 1 is switched on to output a fundamental frequency laser with wavelength of 1064 nm. The fundamental frequency laser is then directed to pass thorough the frequency doubling crystal 2 and the frequency quadrupling crystal 3. As a result, a mixture of lasers comprising laser with wavelength of 1064 nm, 532 nm and 266 nm is obtained, which is further directed to the light filter unit 4. The 1064 nm fundamental frequency laser and 532 nm second harmonic laser are filtered out by the light filter unit 4 thereby resulting in a liner polarized fourth harmonic laser with wavelength of 266 nm as the output of the light filter unit 4. Then, the quarter-wave plate 5 is adjusted such that the pure linear polarized fourth harmonic laser with wavelength of 266 nm is converted into a circular or ellipsometric polarized fourth harmonic laser which is further directed into the Raman cell 6 thorough the first convex lens 11a of the Raman cell 6. The first convex lens 11a is used to focus the circular or ellipsometric polarized fourth harmonic laser with wavelength of 266 nm to the Raman cell 6. The Raman cell 6 is configured to generate different orders of rotational-vibrational stimulated Raman scattering lasers which is directed out of the Raman cell 6 through a second convex lens 11b of the Raman cell 6.

The following is the formula representing different orders of stimulated Raman scattering laser:

$$v_{mn} = v_p + m v_v + n v_R$$

Wherein $v_p$, $v_v$, $v_R$ and $v_{mn}$ denote the frequencies of a pump laser, the vibrational stimulated Raman frequency shift at the predetermined internal pressure, the rotational stimulated Raman frequency shift at a predetermined internal pressure and the frequency of the stimulated Raman scattering laser respectively; m and n denote the orders of vibrational and rotational stimulated Raman frequency shift respectively and m, n=0, ±1, ±2, . . . .

In one embodiment, the frequency of the pump laser $v_p$ is 37,594 cm$^{-1}$ (i.e. 1/266 nm). Furthermore, the vibrational stimulated Raman frequency shift at internal pressure 0.8-1.0 MPa is 2,991 cm$^{-1}$ and the rotational stimulated Raman frequency shift of $H_2$ is 415 cm$^{-1}$.

As circular or ellipsometric polarized fourth harmonic laser is used as the pump laser, both vibrational and rotational stimulated Raman scattering will be stimulated resulting in different orders of stimulated Raman scattering laser. For instance, if m=−1 and n=1, (−1, 1) order rotational-vibrational stimulated Raman scattering laser with frequency $v_{-1,1}$=35,014 cm$^{-1}$ (i.e. with wavelength of 285.6 nm) will be obtained.

The light dispersion device 7 is disposed at the second end of the Raman cell 6, which comprises a plurality of prisms. In one embodiment, the light dispersion device 7 comprises two prisms. By adjusting the angle between two prisms, the rotational-vibrational stimulated Raman scattering light from the Raman cell 6 is spatially separated with different propagation angles (i.e. different light beams at different wavelengths). The optical diaphragm 8 is then positioned at a predefined position to select the laser with desirable wavelength. In one embodiment, the (−1, 1) order rotational-vibrational stimulated Raman scattering light is selected as the Raman laser, i.e. laser with wavelength of 285.6 nm, as it is close to the peak of the excitation spectrum of fluoranthene. Finally, the Raman laser is directed to optical fiber 10 through the convex lens 9 for inducing fluorescence of fluoranthene.

In one embodiment, the output intensity of the 285.6 nm laser can be adjusted through altering the inner pressure of the Raman cell 6 and orientation of the quarter-wave plate 5.

The exemplary embodiments of the present invention are thus fully described. Although the description referred to particular embodiments, it will be clear to one skilled in the art that the present invention may be practiced with variation of these specific details.

What is claimed is:

1. A method of generating Raman laser for inducing fluorescence of fluoranthene comprising the steps of:
    a) emitting a laser beam pulse;
    b) transmitting said laser beam pulse through a frequency doubling crystal and a frequency quadrupling crystal thereby generating a mixture of lasers with different wavelengths;
    c) extracting a pump laser from said mixture of lasers;
    d) passing said pump laser through a quarter-wave plate to change the polarization status of said pump laser;
    e) providing a Raman cell filled with predetermined gas at a predetermined pressure;
    directing said pump laser to said Raman cell thereby exciting different orders of stimulated Raman scattering lasers; and
    g) selecting a predetermined order of said stimulated Raman scattering laser as said Raman laser for inducing fluorescence of fluoranthene.

2. The method as claimed in claim 1, wherein said extracting step further comprising the step of passing said mixture of lasers through a light filter.

3. The method as claimed in claim 1 wherein said predetermined gas is deuterium gas and said predetermined pressure is ranged from 0.8-1.0 MPa.

4. The method as claimed in claim 1, wherein said directing step further comprises the step of directing said pump laser thorough a convex lens before said pump laser reaches said Raman cell.

5. The method as claimed in claim 1, wherein said selecting step further comprises the step of spatially splitting said different orders of stimulated Raman scattering laser.

6. A system of generating Raman laser for inducing fluorescence of fluoranthene comprising:
    a) a pulsed laser source configured to emit a laser beam pulse;
    b) a frequency doubling crystal and a frequency quadrupling crystal for said laser beam pulse to pass thorough thereby generating a mixture of lasers with different wavelengths;
    c) a light filter unit configured to extract a pump laser from said mixture of lasers;
    d) a quarter-wave plate configured to change the polarization status of said pump laser;
    e) a Raman cell filled with predetermined gas at a predetermined pressure configured to generate different orders of stimulated Raman scattering lasers upon interact with said pump laser;
    a light dispersion device configured to split said different orders of stimulated Raman scattering lasers spatially; and
    g) an optical diaphragm configured to select predetermined order of said stimulated Raman scattering laser from said different orders of stimulated Raman scattering lasers.

7. The system of claim 6, wherein said pulsed laser source is a Nd:YAG pulsed laser source.

8. The system of claim 6, wherein said light filter unit further comprises a first light filter and a second light filter, wherein each said first light filter and said second light filter comprises a mirror-like surface which is highly reflective to said pump laser.

9. The system of claim 8, wherein said first light filter and second light filter are disposed such that said mirror faces are perpendicular to each other.

10. The system of claim 6, wherein said predetermined gas is deuterium gas and said predetermined pressure is ranged from 0.8-1.0 MPa.

11. The system of claim 6, wherein said light dispersion device further comprises at least two prisms configured to receive and spatially separate said different orders of stimulated Raman scattering lasers.

12. The system of claim 11, wherein said light dispersion device comprises two triangular prisms and are disposed such that they are in contact at one of the angles having an adjustable angle between two surfaces of said prisms facing each other.

* * * * *